US011813046B2

(12) United States Patent
Li

(10) Patent No.: US 11,813,046 B2
(45) Date of Patent: Nov. 14, 2023

(54) METHOD OF CUFF STORAGE CASE FOR ELECTRONIC BLOOD PRESSURE MONITOR

(71) Applicant: Ke Li, San Jose, CA (US)

(72) Inventor: Ke Li, San Jose, CA (US)

( * ) Notice: Subject to any disclaimer, the term of this patent is extended or adjusted under 35 U.S.C. 154(b) by 294 days.

(21) Appl. No.: 17/406,088

(22) Filed: Aug. 19, 2021

(65) Prior Publication Data
US 2023/0054507 A1  Feb. 23, 2023

(51) Int. Cl.
*A61B 5/022* (2006.01)
*A61B 5/021* (2006.01)

(52) U.S. Cl.
CPC ...... *A61B 5/02233* (2013.01); *A61B 5/02141* (2013.01)

(58) Field of Classification Search
CPC . A61B 5/02141; A61B 5/022; A61B 5/02208; A61B 5/02225; A61B 5/02233; A61B 5/02241; A61B 5/0225; A61B 17/132
USPC .......................... 600/485, 490, 493; 206/305
See application file for complete search history.

(56) References Cited

U.S. PATENT DOCUMENTS

| | | | | |
|---|---|---|---|---|
| 3,911,904 A * | 10/1975 | Saba | ....................... | A61B 5/023 600/490 |
| 6,019,730 A * | 2/2000 | Rashman | ............... | A61B 5/023 600/490 |
| 6,344,025 B1 * | 2/2002 | Inagaki | .............. | A61B 5/02233 600/490 |
| 6,575,904 B2 * | 6/2003 | Nagai | .................. | A61B 5/0013 345/169 |
| 2004/0167408 A1 * | 8/2004 | Ashida | ................... | G16H 10/60 206/538 |
| 2005/0126938 A1 * | 6/2005 | Uehata | ............... | G01N 33/4875 435/14 |
| 2006/0064022 A1 * | 3/2006 | Yang | ...................... | A61B 5/022 600/490 |
| 2007/0038133 A1 * | 2/2007 | Kishimoto | ............. | A61B 5/022 600/490 |
| 2007/0197923 A1 * | 8/2007 | Kishimoto | ............. | A61B 5/022 600/490 |
| 2009/0062664 A1 * | 3/2009 | Chang | ................ | A61B 5/02233 600/300 |

(Continued)

FOREIGN PATENT DOCUMENTS

| | | | |
|---|---|---|---|
| JP | 2006271408 A | * | 10/2006 |
| JP | 2009225865 A | * | 10/2009 |
| JP | 2011125627 A | * | 6/2011 |

*Primary Examiner* — Joshua E Rodden
(74) *Attorney, Agent, or Firm* — Ke Li

(57) ABSTRACT

A method of cuff storage case for an electronic blood pressure monitor includes an electronic blood pressure monitor main part, cuff, and a cuff storage case. One end of the air tube connects to a side of the electronic blood pressure monitor main part, and the other end of the air tube connects to a cuff. When the electronic blood pressure monitor main part is not in use, the cuff can place inside the cuff storage case. The Cuff storage case connects to the electronic blood pressure monitor main part through the connecting element. The cuff storage case fixes on the electronic blood pressure monitor main part through the connecting element and will not restrict the models and shapes of the electronic blood pressure monitor. It can apply to most kinds of electronic blood pressure monitors.

3 Claims, 4 Drawing Sheets

(56) References Cited

U.S. PATENT DOCUMENTS

| | | | |
|---|---|---|---|
| 2011/0301476 A1* | 12/2011 | Sawanoi | A61B 5/02225 600/494 |
| 2012/0220885 A1* | 8/2012 | Fumuro | A61B 50/31 206/363 |
| 2019/0076034 A1* | 3/2019 | Mori | A61B 5/02125 |
| 2023/0054507 A1* | 2/2023 | Li | A61B 5/02141 |

* cited by examiner

METHOD OF CUFF STORAGE CASE FOR ELECTRONIC BLOOD PRESSURE MONITOR

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention generally relates to an electronic blood pressure monitor's cuff storage case and more specifically relates to a cuff storage case for most electronic blood pressure monitors.

2. Description of the Related Art

The electronic blood pressure monitor is a medical device that uses current electronic technology and indirect blood pressure measurement methods to measure blood pressure. The devices usually consist of a cuff, a sensor, an inflator, and the measure electro circuit. Furthermore, it uses oscillometric method, auscultatory method, or similar non-invasive blood pressure measurement method to measure the blood pressure.

The cuff of the electronic blood pressure monitor separates from the main part of the electronic blood pressure monitor and connects to the electronic blood pressure monitor main part by an air tube. Therefore, when people sort out the electronic blood pressure monitor, the cuff will be placed close to the electronic blood pressure monitor main part at random, making it look messy. Only a few electronic blood pressure monitors in the market come with the cuff storage case. However, those cuff storage cases have a unique structure and can only be used for the assigned electronic blood pressure monitors model and cannot be universal. Given the above problems, a solution proposes below. According to the present invention, a new cuff storage case substantially departs from the conventional concepts and designs of the prior art. In so doing provides an apparatus primarily developed to efficiently store the cuff for most kinds of electronic blood pressure monitors.

BRIEF SUMMARY OF THE INVENTION

The purpose of this invention is to provide a cuff storage case for electronic blood pressure monitors, which has the advantages of applying to most kinds of electronic blood pressure monitors, simple structure, and is easy to install.

The above purpose of the present invention is achieving by following technical solutions.

A method of a cuff storage case for an electronic blood pressure monitor includes an electronic blood pressure monitor main part, cuff, and a cuff storage case. There is an air tube, one end of the air tube connects to a side of the electronic blood pressure monitor main part, and the other end of the air tube connects to a cuff. When an electronic blood pressure monitor is not in use cuff will be placed inside the cuff storage case. There is a connecting element between the electronic blood pressure monitor main part and cuff storage case that connects the electronic blood pressure monitor main part and cuff storage case together. The connecting element includes a junction plate and a fixed buckle, and the junction plate fixed to one side the electronic blood pressure monitor's main part, the fixed buckle fixed to a side of the cuff storage case. There is a notch at the bottom of the fixed buckle, which pairs with the junction plate. Stuck the junction plate into the notch, and the fixed buckle will slide fit with the junction plate.

The main part of the cuff storage case is a storage groove; The shape of the upper part of the storage groove is the funnel. The cuff of the electronic blood pressure monitor can directly insert into the cuff storage case after simply rolling up the cuff.

A tube groove provides on one side of the cuff storage case, and the air tube directly into the cuff storage case through the tube groove.

The edges and corners of the cuff storage case are rounded.

BRIEF SUMMARY OF THE INVENTION

The benefits of this invention are as follows: Insert the junction plate into the notch make the fixation between the cuff storage case and the electronic blood pressure monitor main part. The cuff of the electronic blood pressure monitor can directly insert into the cuff storage case after simply rolling up the cuff to achieve the storage of the cuff.

BRIEF SUMMARY OF THE DRAWING

Various other objects, features, and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
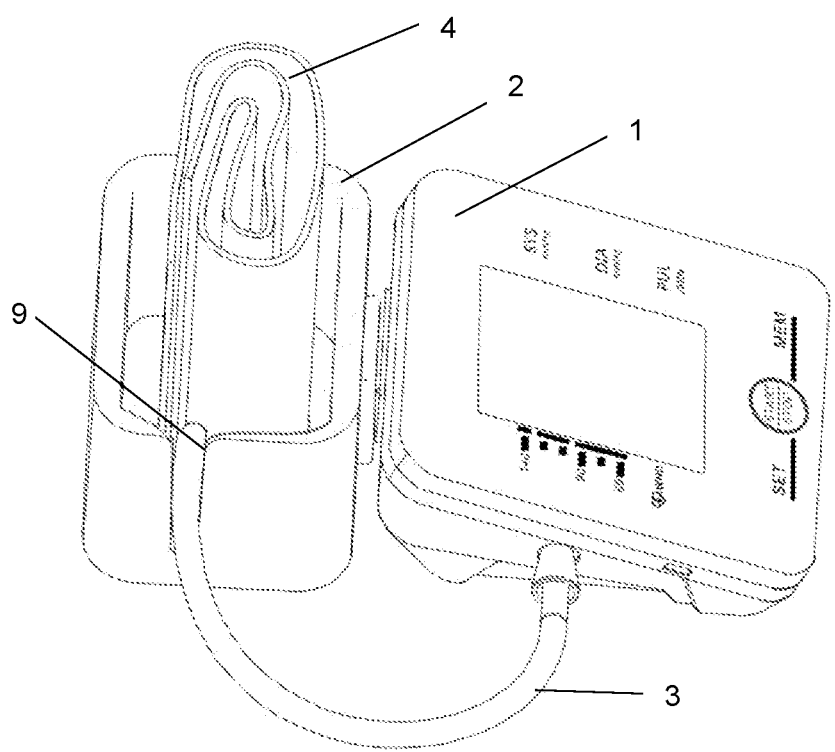
FIG. 1 is a side schematic view of invention.

The following descriptions are only preferred methods of the present invention, and the scale of protection is not limited to this preferred method. All technical solutions that follow the idea of the present invention should belong to the scale of protection of the present invention.

The same drawing indicates the same parts. Note that the terms 'front', 'back,' 'left,' 'right,' 'upper' and 'bottom' used in the following description refer to the directions in the drawings.

As shown in FIG. 1, a method of cuff storage case for an electronic blood pressure monitor includes an electronic blood pressure monitor main part 1, cuff 4, and a cuff storage case 2. One end of the air tube 3 connects to a side of the electronic blood pressure monitor main part 1, and the other end of the air tube 3 connects to the cuff 4. There is a connecting element between electronic blood pressure monitor main part 1 and cuff storage case 2 uses to connect electronic blood pressure monitor main part 1 and cuff storage case 2. Cuff 4 of the electronic blood pressure monitor can directly insert into the cuff storage case 2 after simply rolling up the cuff 4 to achieve the storage of the cuff 4.

Figure 2:
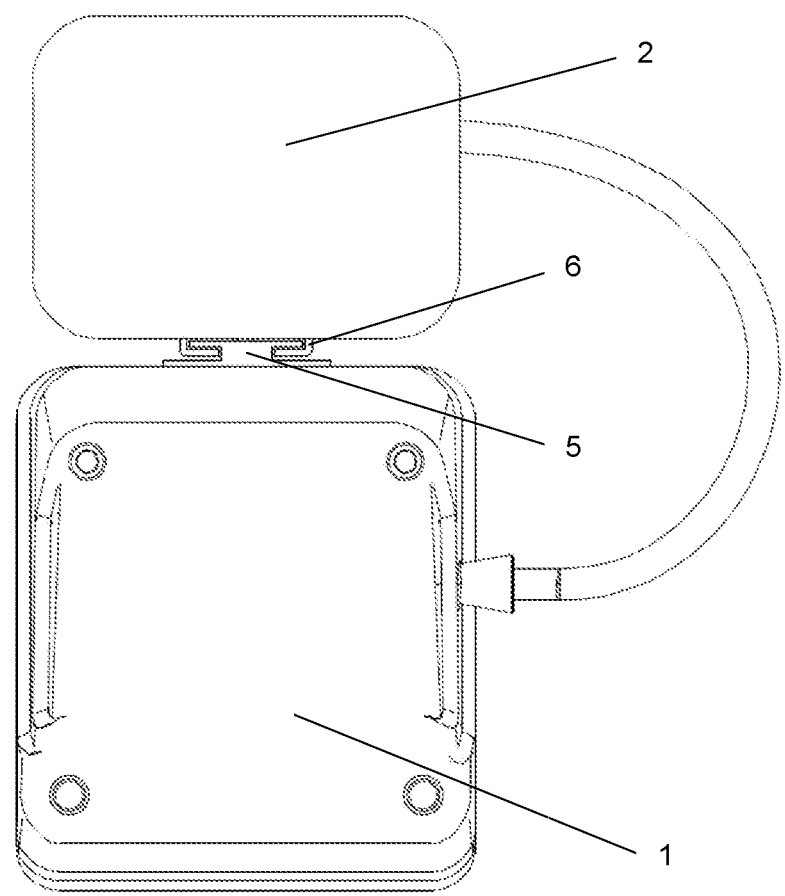
FIG. 2 is a bottom schematic view of invention.
Figure 3:
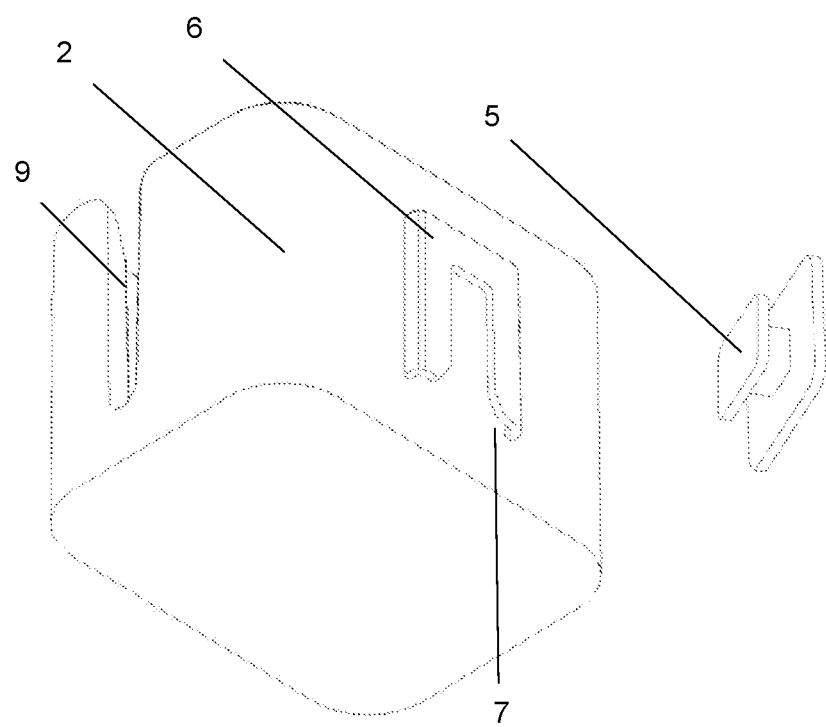
FIG. 3 is a schematic view of connecting element.

As shown in FIG. 2 and FIG. 3 the connecting element includes a junction plate 5 and a fixed buckle 6. The junction plate 5 fixes to the sidewall of the electric blood pressure monitor main part 1, and the fixed buckle 6 fixes to the sidewall of the cuff storage case 2. The cross-section of junction plate 5 is I-shaped. Moreover, the bottom of the fixed buckle 6 is a notch 7. Place the fixed buckle 6 on the upper end of the junction plate 5 and move it down so that the junction plate 5 sets into notch 7.

Figure 4:
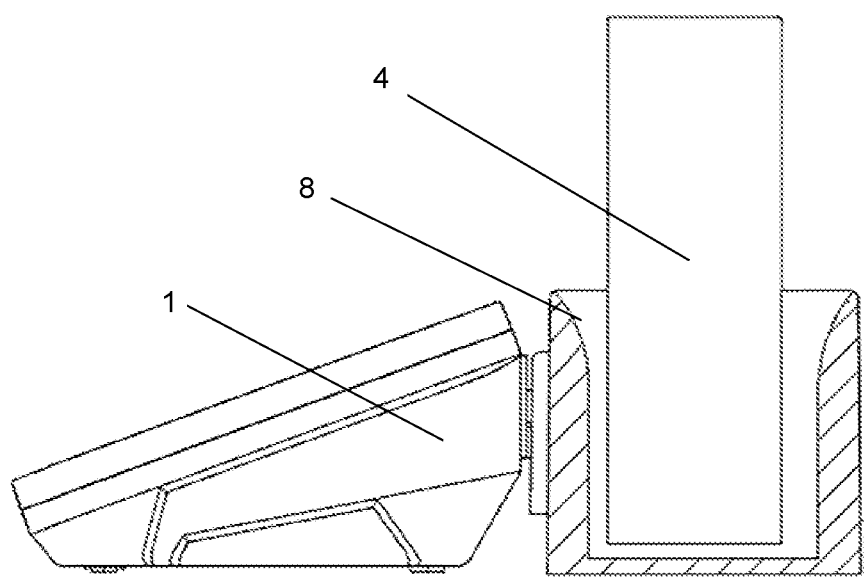
FIG. 4 is a section view of invention.
1: Electronic blood pressure monitor main part
2: Cuff storage case.
3: Air tube.
4: Cuff
5: Junction plate
6: Fixed buckle
7: Notch
8: Storage groove
9: Tube groove

As shown in FIG. 1, FIG. 3 and FIG. 4, The main part of the cuff storage case 2 is a storage groove 8; The shape of the upper part of the storage groove 8 is a funnel, and the rest part is cuboid. The width of the upper end of the storage case 2 is larger than the bottom. After simply rolling up cuff 4, the user can easily set the cuff 4 into the storage case 2.

As shown in FIG. 1 and FIG. 3, one side of cuff storage case 2 has a tube groove 9, and air tube 3 passes through tube groove 9 into the cuff storage case 2. The edges and corners of cuff storage case 2 rounded to prevent injury and made the cuff storage case looks beautiful.

This invention's principle is to set junction plate 5 into notch 7 to connect junction plate 5 and the fixed buckle 6. In this way, cuff storage case 2 can connect the electronic blood pressure monitor's main part 1. The cuff can insert into the cuff storage after simply rolling up the cuff to achieve the storage of the cuff 4.

I claim:

1. A method of cuff storage for an electronic blood pressure monitor comprising:
   an electronic blood pressure monitor main part, a cuff and a cuff storage case;
   one end of an air tube connects to a side of the electronic blood pressure monitor main part, and another end of the air tube connects to the cuff;
   a connecting element between the electronic blood pressure monitor main part and the cuff storage case which is used to removably connect the electronic blood pressure monitor main part and the cuff storage case;
   the cuff storage case includes a storage groove, a shape of an upper part of the storage groove is a funnel, and a shape of a lower part is cuboid, such that a width of the upper part of the storage groove is larger than a width of the lower part of the storage groove; and
   the cuff of the electronic blood pressure monitor main part configured to be directly inserted into the cuff storage case after rolling up the cuff to achieve storage of the cuff.

2. The method of cuff storage for the electronic blood pressure monitor of claim 1, wherein one side of the cuff storage case has a tube groove, and the air tube passes through the tube groove into the cuff storage case.

3. The method of cuff storage for the electronic blood pressure monitor of claim 1, wherein edges and corners of the cuff storage case are rounded to prevent injury and make the cuff storage case look beautiful.

* * * * *